(12) United States Patent
Klaue

(10) Patent No.: US 6,454,770 B1
(45) Date of Patent: Sep. 24, 2002

(54) SYMMETRICAL BONE PLATE

(75) Inventor: Kaj Klaue, Bern (CH)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/518,780

(22) Filed: Mar. 3, 2000

Related U.S. Application Data

(63) Continuation-in-part of application No. PCT/CH97/00323, filed on Sep. 4, 1997.

(51) Int. Cl.⁷ .................................................. A61B 17/80
(52) U.S. Cl. ........................................... 606/69; 606/73
(58) Field of Search ............................. 606/61, 69, 70, 606/71, 62, 64; 623/16.11

(56) References Cited

U.S. PATENT DOCUMENTS

| | | | |
|---|---|---|---|
| 2,133,859 A | * | 10/1938 | Hawley |
| 2,614,559 A | * | 10/1952 | Livingston |
| 3,463,148 A | | 8/1969 | Treace |
| 4,403,606 A | * | 9/1983 | Woo et al. |
| 4,790,302 A | * | 12/1988 | Colwill et al. |
| 4,836,196 A | * | 6/1989 | Park et al. |
| 4,838,252 A | * | 6/1989 | Klaue |
| 5,209,751 A | * | 5/1993 | Farris et al. .................. 606/61 |
| 5,487,741 A | * | 1/1996 | Maruyama et al. ........... 606/60 |
| 5,709,686 A | * | 1/1998 | Talos et al. .................... 606/69 |

FOREIGN PATENT DOCUMENTS

| | | |
|---|---|---|
| FR | 2 642 958 | 8/1990 |
| FR | 2 680 673 | 3/1993 |
| WO | WO 90/07304 | 7/1990 |

* cited by examiner

*Primary Examiner*—David O. Reip
(74) *Attorney, Agent, or Firm*—Pennie & Edmonds LLP

(57) ABSTRACT

The invention relates to a bone plate that has a longitudinal axis, top and bottom surfaces and plate holes which extend between the two surfaces for receiving bone screws or other fasteners. The bone plate is substantially symmetrical about a middle plane extending between the two surfaces. The symmetry of the bone plate makes it possible to set the bone plate on and fasten it to the bone with either surface facing the bone without affecting the clinical results.

12 Claims, 4 Drawing Sheets

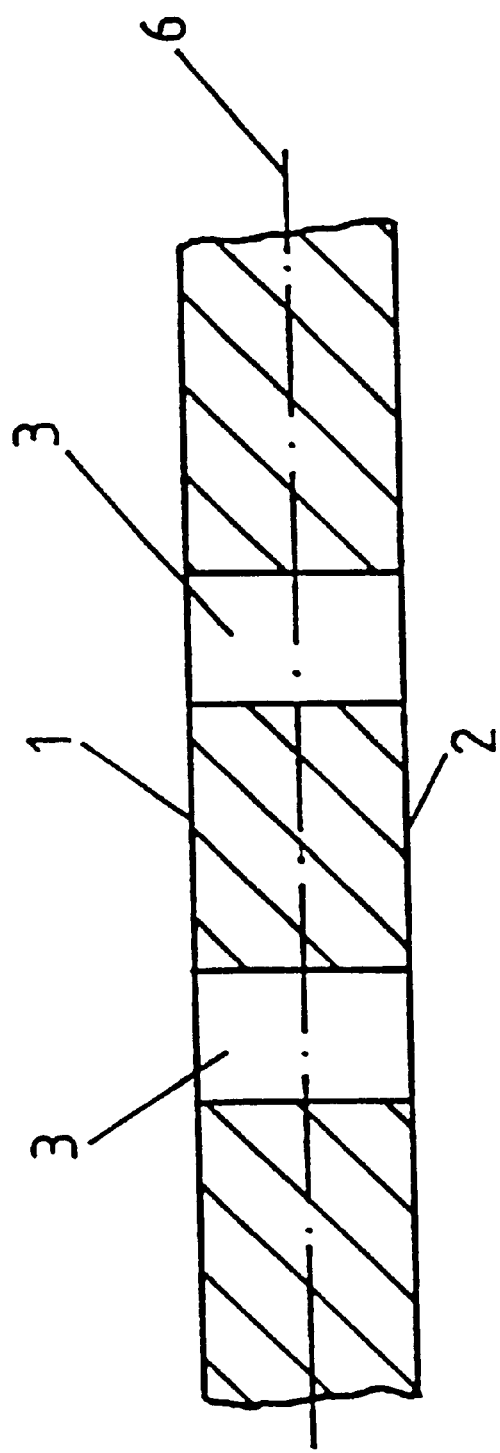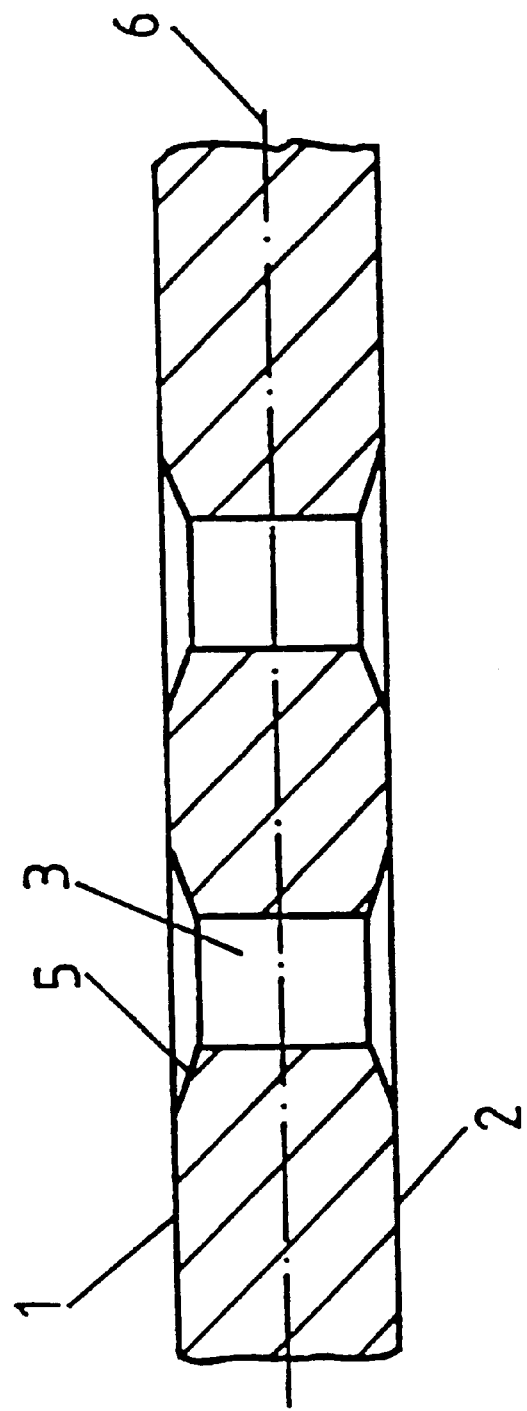

SYMMETRICAL BONE PLATE

CROSS-REFERENCE TO RELATED APPLICATIONS

This application is a continuation-in-part of the U.S. national stage designation of copending International Patent Application PCT/CH97/00323, filed Sep. 4, 1997, the entire content of which is expressly incorporated herein by reference thereto.

FIELD OF THE INVENTION

The invention relates to a bone plate and bone plate/fastener combination for fracture fixation and methods for using the same.

BACKGROUND OF THE INVENTION

A large number of bone plates are known from the prior art. The vast majority of these plates are designed with a bottom side intended for surface contact with the bone. In contrast, the top side of the plate is not designed for this surface contact and usually has countersunk areas in the plate holes to better accommodate the heads of the bone screws. Because of the different features for the top and bottom surfaces of the bone plate, most prior art bone plates are asymmetrical with regard to their main middle plane, i.e. a plane extending between the top and bottom surfaces.

The disadvantages of these asymmetric bone plates include the fact that for optimal clinical results, the plate must be secured to the bone with the bottom surface in contact with the bone. However, clinical experience has shown that in the operating room, bone plates are occasionally applied to the bone with the wrong side facing the bone. Such errors are more likely to occur when working with bone plates having small dimensions and when the operating personnel are pressed for time.

French Patent No. 2,642,958 discloses a spinal bone plate that appears to have plate holes that are countersunk on both the top and bottom surfaces. However, the bone plate also appears to have a longitudinal curvature, and is therefore asymmetrical. French Patent No. 2,680,673 discloses another spinal bone plate. The bone plate, which also appears to have plate holes that are countersunk on both the top and bottom surfaces, contradicts the type of use given in the description for the lumbar spine, which would require an anatomical curvature of approximately 158°. The rectangular profile shown in both of these French patents is also not optimal for some clinical applications.

Thus, there exists a need for an improved bone plate.

SUMMARY OF THE INVENTION

The present invention is directed to a bone plate having first and second surfaces and at least one plate hole extending from the first surface to the second surface for receiving a fastener, such as a bone screw. The bone plate has a cross section that is preferably oval. The bone plate is substantially symmetrical about a middle plane extending between the first and second surfaces. Because the bone plate is substantially symmetrical, a first volume ($V_a$) defined by a portion of the bone plate from the first surface to the middle plane and a second volume ($V_b$) defined by a portion of the bone plate from the second surface to the middle plane are configured and dimensioned such that $V_a/V_b$ is between about 0.98 and 1.02.

Advantageously, the plate holes can be cylindrical and round. Also, the plate holes may be narrower in a central portion and wider in end portions that extend toward the first and second surfaces, i.e. the plate holes are countersunk on each end. If the plate holes are countersunk, the end portions preferably have a conical shape toward the first and second surfaces. In an exemplary embodiment, the diameter of the plate holes in a direction parallel to the longitudinal axis of the bone plate is greater than the diameter in a direction perpendicular to the longitudinal axis. In this exemplary embodiment, the plate holes preferably have an oval shape.

In one embodiment, the first and second surfaces may be planar. In another embodiment, the first and second surfaces are advantageously concave along the longitudinal axis in an area between consecutive plate holes.

The bone screw can have a spherical head for slidingly engaging the plate holes. In order to lock the bone screw to the bone plate, the bone screw can have a thread engaging the plate holes.

The present invention also relates to a method for fixing a bone with a bone plate having first and second surfaces and at least one plate hole extending from the first surface to the second surface. A section of the bone plate is attached to a first portion of the bone such that the first surface of the bone plate faces the first portion of the bone. Another section is attached to a second portion of the bone such that the second surface of the bone plate faces the second portion of the bone.

In another method according to the present invention, a first portion of the bone plate is inserted into the medullary canal of the bone and a second portion of the bone plate is attached to the cortex of the bone. Because of the structure of the bone plate according to the present invention, either the first or second surface of the second portion can face the cortex of the bone.

BRIEF DESCRIPTION OF THE DRAWINGS

Preferred features of the present invention are disclosed in the accompanying drawings, wherein similar reference characters denote similar elements throughout the several views, and wherein:

FIG. 2 shows a longitudinal section through the bone plate of FIG. 1;

FIG. 3 shows a longitudinal section through a bone plate according to the present invention with slightly countersunk plate holes;

DETAILED DESCRIPTION OF THE INVENTION

Figure 1:
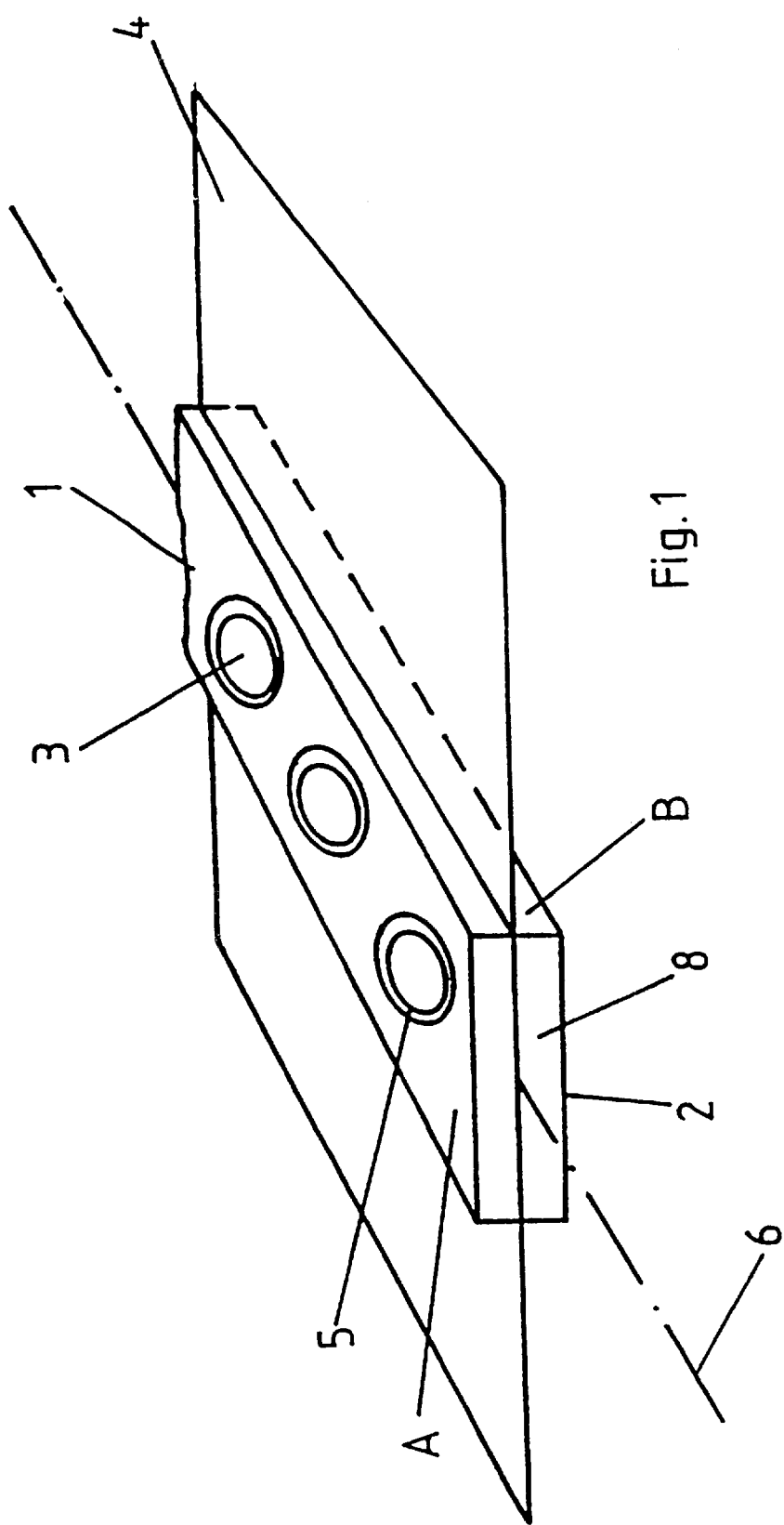
FIG. 1 shows a perspective view of a bone plate according to the present invention having a rectangular cross section.

As shown in FIG. 1, a bone plate according to the present invention has a longitudinal axis 6, two surfaces 1, 2 (first surface 1 and second surface 2), and plate holes 3. Plate holes 3 extend from first surface 1 through second surface 2 for accommodating fasteners, e.g. bone screws 7 (FIG. 5), to secure the bone plate to the bone. A middle plane 4 divides the bone plate into two substantially symmetrical halves A and B and runs between first and second surfaces 1, 2. Minor deviations from the symmetry of halves A and B of the bone plate bordered by the plane of symmetry are allowed, but the deviations should be such that the volumes $V_a$ and $V_b$ are in the range of $0.98 < V_a/V_b < 1.02$, preferably $0.99 < V_a/V_b < 1.01$.

Figure 5:
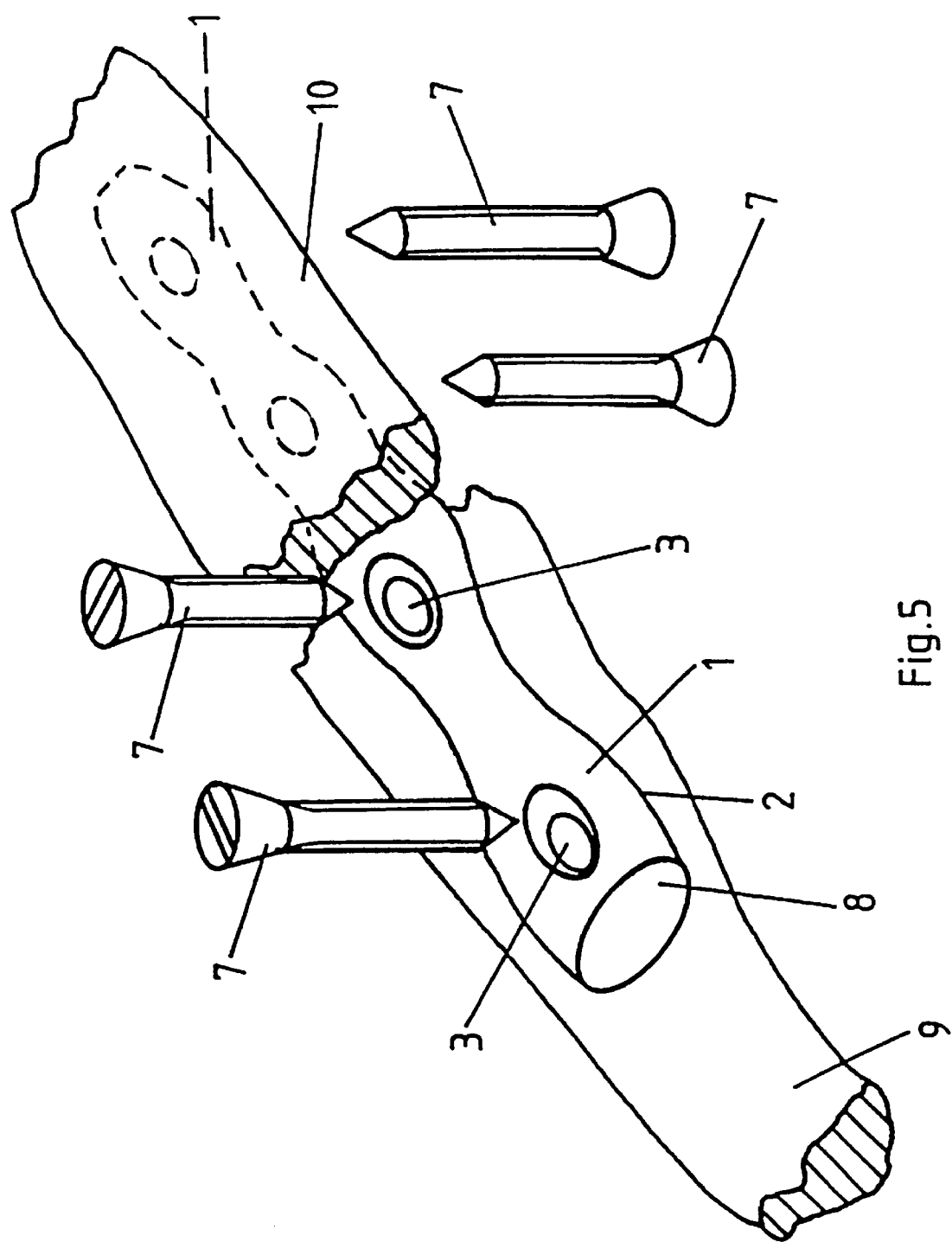
FIG. 5 shows a perspective view of bone plate according to the present invention having an oval cross section.

The bone plate shown in FIG. 1 has a rectangular cross section. In other words, the profile 8 running perpendicular to the longitudinal axis 6 is rectangular. Alternatively, as shown in FIG. 5, the profile can be oval. As discussed in more detail below, the oval geometry may be beneficial in certain clinical applications.

As shown in FIG. 2, plate holes 3 may be round and cylindrical. This geometry minimizes the change in material properties in the areas near the plate holes. With other embodiments, e.g. according to FIGS. 3 and 4, plate holes 3 are countersunk toward both the first and second surfaces 1, 2. Countersink plate holes 3 better accommodate the heads of the bone screws. In an exemplary embodiment, the countersinks are in the shape of a cone 5.

In the embodiment shown in FIG. 1, first and second surfaces 1, 2 are planar. In the embodiment shown in FIG. 5, however, first and second surfaces 1, 2 are each designed to be concave in the area between plate holes 3. This geometry reduces the rigidity in the area between plate holes 3. As the area near plate holes 3 already has reduced rigidity because of the plate holes, the geometry shown in FIG. 5 achieves a uniform rigidity of the bone plate.

Figure 4:
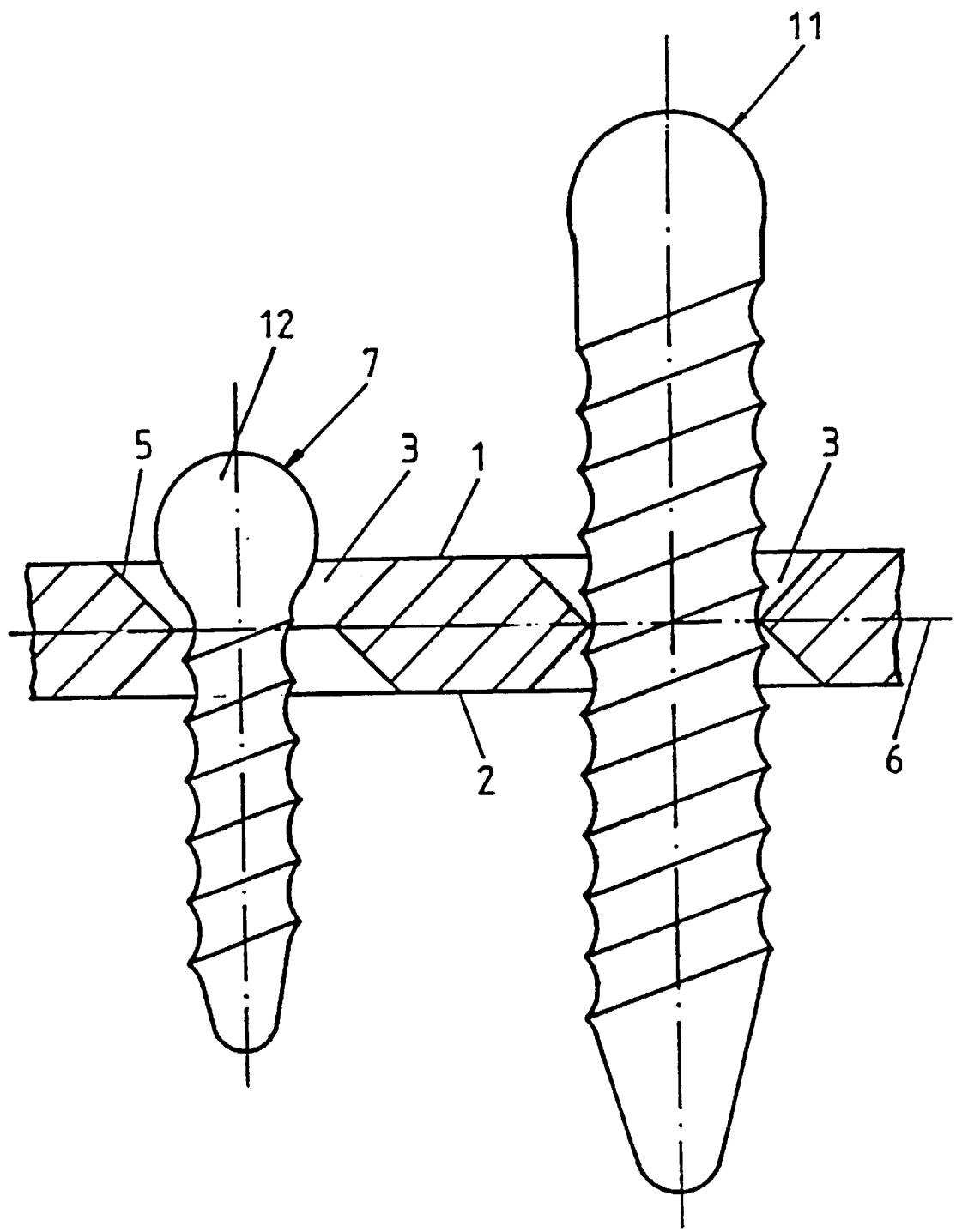
FIG. 4 shows a longitudinal section through a bone plate according to the present invention with larger countersunk plate holes and two types of screws.

FIG. 4 shows two types of bone screws 7 and 11 having different functions. Bone screw 7, shown at the left of the figure, is a screw for fixation of the bone plate. The diameter of its thread is smaller than the narrowest point in plate hole 3, so that it does not engage plate hole 3. Head 12 of bone screw 7 is spherical in shape, so that it can slide optimally in cone 5 of plate hole 3. Bone screw 11, shown at the right in the figure, is a screw for locking the bone place. The diameter of its thread is larger than the narrowest point in plate hole 3, so that it laterally engages plate hole 3.

Because of the symmetry of the bone plate according to the present invention, the bone plate can be attached with either first or second surface 1, 2 facing the bone with identical clinical results. The symmetry is also useful for certain clinical situations. For example, the same bone plate can be used to fix two bone fragments with the first surface 1 contacting one of the bone fragments at one end and the second surface 2 contacting the other bone fragment at the other end. FIG. 5 shows one application of the bone plate in which the front part with one surface 2 is attached to the front bone fragment 9 by means of two bone screws 7, and the rear part with the other surface 1 is attached to the rear bone fragment 10 with two bone screws 7. The bone plate and screws thereby form a "Z" shape. Such an application is of interest when one end of the plate is completely inserted into the medullary canal of one of the bone fragments and the other end is attached to the cortex of the other fragment, or in the case of an osteotomy, when a shift by one entire bone width is to be achieved. Thus, in these situations, the bone plate functions as an extra-medullary and intra-medullary device, i.e. as both a nail and a plate. Because of the shape of the medullary canal, the oval cross section of the bone plate in FIG. 5 is particular suited for insertion in the medullary canal.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. For example, the cross section of the bone plate may be rectangular or arcuate in configurations that are other than the preferred oval shape. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A bone plate having a longitudinal axis and comprising first and second surfaces, a middle plane extending between the first and second surfaces and a plurality of plate holes extending from the first surface to the second surface for receiving a fastener, wherein the bone plate has an oval cross section and is configured and dimensioned to be substantially symmetrical about the middle plane, and wherein the first and second surfaces are concave along the longitudinal axis in an area between consecutive plate holes.

2. The bone plate of claim 1, wherein at least one plate hole is cylindrical.

3. The bone plate of claim 1, wherein at least one plate hole has a relatively narrow central portion and end portions that widen as they extend toward the first and second surfaces.

4. The bone plate of claim 3, wherein at least one plate hole has a relatively narrow central portion and end portions that have a conical cross section extending toward the first and second surfaces.

5. The bone plate of claim 1, wherein the diameter of at least one plate hole in a direction parallel to the longitudinal axis is greater than the diameter in a direction perpendicular to the longitudinal axis.

6. The bone plate of claim 5, wherein at least one plate hole has an oval shape.

7. The bone plate of claim 1 wherein a first volume ($V_a$) defined by a portion of the bone plate from the first surface to the middle plane and a second volume ($V_b$) defined by a portion of the bone plate from the second surface to the middle plane are configured and dimensioned such that $V_a/V_b$ is between about 0.98 and 1.02.

8. The bone plate of claim 1, in combination with a bone screw fastener.

9. The bone plate of claim 8, wherein the bone screw has a spherical head for slidingly engaging at least one plate hole.

10. The bone plate of claim 8, wherein the bone screw has a thread engaging at least one plate hole for locking the bone screw to the bone plate.

11. A method for fixing a bone with a bone plate having first and second surfaces and at least one plate hole extending from the first surface to the second surface for receiving a fastener, the method comprising the steps of:

attaching the bone plate to a first portion of the bone such that the first surface of the bone plate faces the first portion of the bone; and attaching the bone plate to a second portion of the bone such that the second surface of the bone plate faces the second portion of the bone, wherein the bone plate has an oval cross section and wherein the first and second surfaces are adapted and configured for contact with an external bone surface.

12. A method for fixing a bone having a cortex and a medullary canal with a bone plate having first and second surfaces and at least one plate hole extending from the first surface to the second surface for receiving a fastener, the method comprising the steps of:

inserting a first portion of the bone plate into the medullary canal of the bone; and attaching a second portion of the bone plate to the cortex of the bone outside the medullary canal, wherein either the first or second surface of the second portion can face the cortex of the bone, and both the first and second portions of the bone plate have at least one plate hole for receiving a fastener.

* * * * *